(12) United States Patent
Fujiyama et al.

(10) Patent No.: US 7,993,586 B2
(45) Date of Patent: Aug. 9, 2011

(54) APPARATUS FOR MEASUREMENT OF TOTAL ORGANIC CARBON CONTENT

(75) Inventors: Yoichi Fujiyama, Kyoto (JP); Masakazu Akechi, Kyoto (JP); Masaki Kanai, Kyoto (JP)

(73) Assignee: Shimadzu Corporation, Kyoto (JP)

( * ) Notice: Subject to any disclaimer, the term of this patent is extended or adjusted under 35 U.S.C. 154(b) by 474 days.

(21) Appl. No.: 11/770,080

(22) Filed: Jun. 28, 2007

(65) Prior Publication Data

US 2009/0004061 A1 Jan. 1, 2009

(51) Int. Cl.
*G01N 21/00* (2006.01)
*G01N 31/12* (2006.01)
*G01N 15/06* (2006.01)
*G01N 33/00* (2006.01)
*G01N 33/48* (2006.01)

(52) U.S. Cl. ........ 422/82.05; 422/68.1; 422/78; 422/79; 436/146

(58) Field of Classification Search ................ 422/82.05
See application file for complete search history.

(56) References Cited

U.S. PATENT DOCUMENTS

| | | | |
|---|---|---|---|
| 5,132,094 A * | 7/1992 | Godec et al. | 422/68.1 |
| 5,443,991 A | 8/1995 | Godec et al. | |
| 5,750,073 A * | 5/1998 | Godec et al. | 422/79 |
| 6,444,474 B1 * | 9/2002 | Thomas et al. | 436/146 |

FOREIGN PATENT DOCUMENTS

JP 2001-281189 A 10/2001

OTHER PUBLICATIONS

"Laminate," online Wikipedia article, Dec. 2009.*

* cited by examiner

*Primary Examiner* — Sam P Siefke
*Assistant Examiner* — Bryan Kilpatrick
(74) *Attorney, Agent, or Firm* — Sughrue Mion, PLLC

(57) ABSTRACT

Disclosed is a total organic carbon (TOC) measurement apparatus capable of facilitating reduction in size of the apparatus and achieving enhanced measurement accuracy. The TOC measurement apparatus includes an organics oxidation unit, a carbon-dioxide separation unit and a conductivity measurement unit, which are integrally formed by laminating a plurality of plates to define therebetween and incorporate therein an oxidizing flow passage, an aqueous-sample flow passage, a gas permeable membrane, a measurement-water flow passage and a conductivity measuring electrode. The TOC measurement apparatus is designed such that carbon oxide in an aqueous sample is transferred from the aqueous-sample flow passage to the measurement-water flow passage through the gas permeable membrane, and a conductivity of measurement water which contains the carbon oxide and flows through a flow passage facing the conductivity measuring electrode is determined and converted to a TOC content.

5 Claims, 2 Drawing Sheets

APPARATUS FOR MEASUREMENT OF TOTAL ORGANIC CARBON CONTENT

BACKGROUND OF THE INVENTION

1. Field of the Invention

The present invention relates to a total organic carbon measurement apparatus for determining a total organic carbon (TOC) content in an aqueous sample, and more particularly to a total organic carbon measurement apparatus designed to separate organic substances contained in low-impurity water, called "pure water" or "ultra-pure water", through a carbon-dioxide separation unit, and determine a TOC content of the water based on conductivity.

2. Description of the Related Art

With a view to water quality management, a sample of low-impurity water, such as pharmaceutical waters, semiconductor manufacturing process waters, cooling waters, boiler waters or drinking waters, is subjected to TOC measurement to measure organics contained therein.

There has been known a TOC measurement method which comprises the steps of: converting organic compounds in an aqueous sample to carbon dioxide by an oxidation reactor; passing the aqueous sample containing the carbon dioxide into a carbon-dioxide detection mechanism including a conductivity measurement device, through a gas permeable membrane selective for passage of carbon dioxide; and measuring a conductivity of the aqueous sample by the carbon-dioxide detection mechanism [see JP 2510368B or corresponding U.S. Pat. No. 5,443,991].

In the TOC measurement method, a technique of measuring a conductivity of a carbon dioxide-containing aqueous sample includes arranging at least two electrodes at respective positions before and after oxidation of organic compounds in an aqueous sample, to detect a difference between conductivities before and after the oxidation (see JP 2001-281189A).

One such example is A-1000 TOC analyzers produced by Anatel Corporation.

There has also been known a technique of providing a carbon-dioxide separation unit adapted to transfer only carbon dioxide from an aqueous sample to measurement water, measuring a conductivity of the measurement water containing the carbon dioxide, and determining a TOC content of the aqueous sample according to calculation based on the measured conductivity, to reduce the influence of ionic impurities so as to provide a relatively small TOC measurement apparatus with enhanced measurement accuracy. One such example is Sievers® Series TOC Analyzers produced by GE Analytical Instruments.

In the configurations of the above apparatuses, it is necessary to provide flow passages for the aqueous sample and the measurement water, and therefore various pipes made of different materials have to be used for connecting the organics oxidation unit, the carbon-dioxide transfer/separation unit and the conductivity measurement unit. Thus, these apparatuses are likely to be affected by contamination due to elution of the pipe materials or the like.

Moreover, in these apparatuses, each component is apt to become larger in size, which leads to an increase in consumption of the aqueous sample and the measurement water. Thus, it is required to take measures to reduce the consumption of the aqueous sample and the measurement water, such as addition of an acid for facilitating transfer of dissolved carbon dioxide and/or an oxide (e.g., potassium peroxodisulfate) for ensuring decomposition of organics.

Although microfabrication techniques may be utilized to facilitate reduction in size of the apparatus so as to reduce the consumption of the aqueous sample and the measurement water, a flow rate thereof will be undesirably lowered.

Specifically, if the TOC measurement apparatus is downsized using microfabrication techniques to reduce the consumption of the sample and the reagents, the influence of eluates from the pipe materials and/or carbon dioxide to be transferred will become more prominent along with a resulting decrease in flow rate of the liquid.

SUMMARY OF THE INVENTION

In view of the above problems, it is an object of the present invention to provide a total organic carbon measurement apparatus capable of facilitating reduction in size of the apparatus and achieving enhanced measurement accuracy.

In order to achieve this object, the present invention provides a total organic carbon measurement apparatus which comprises an organics oxidation unit for oxidizing and converting organics in an aqueous sample supplied thereinto, to carbon dioxide, a carbon-dioxide separation unit for transferring the carbon dioxide in the aqueous sample after passing through the organics oxidation unit, to measurement water, and a conductivity measurement unit for measuring a conductivity of the measurement water from the carbon-dioxide separation unit. The carbon-dioxide separation unit includes a gas permeable membrane, a first plate and a second plate which are laminated and fixed to each other in such a manner that an aqueous-sample flow passage is defined between the first plate and the gas permeable membrane, and a measurement-water flow passage is defined between the second plate and the gas permeable membrane and in opposed relation to the aqueous-sample flow passage through the gas permeable membrane.

In the total organic carbon measurement apparatus of the present invention, the conductivity measurement unit may include a third plate fixedly attached to the second plate in opposed relation thereto in such a manner that the third and second plates are arranged to define therebetween a measurement cell in fluid communication with the measurement-water flow passage, and a conductivity measuring electrode disposed in the measurement cell. The fluid communication between the measurement-water flow passage and the measurement cell may be provided through a through-hole formed in the second plate.

If carbon dioxide in ambient air or the like is dissolved in the aqueous sample, a TOC content in the aqueous sample will be undesirably changed. Thus, it is necessary to quickly subject the aqueous sample to the TOC measurement. From this point of view, the organics oxidation unit preferably includes a fourth plate fixedly attached to the first plate in opposed relation thereto. In this case, the fourth and first plates are arranged to define therebetween an oxidizing flow passage in fluid communication with the aqueous-sample flow passage, and the fourth plate is made of a transparent material which allows external ultraviolet light to enter at least a part of the oxidizing flow passage, whereby organics in the aqueous sample is oxidized by irradiation of ultraviolet light.

The fluid communication between the aqueous-sample flow passage and the oxidizing flow passage may be provided through a through-hole formed in the first plate.

Circulating water for the measurement water, such as ion-exchanged water, has an optimal flow rate for maintaining background characteristics thereof. However, if the ion-exchanged water is set at its optimal flow rate (e.g. 2 mL/min), the flow rate will deviate from a flow rate (e.g., 0.1 mL/min) of the measurement water suitable for the conductivity measurement. From this point of view, the second and third plates may be arranged to define therebetween a branch flow passage for guiding a part of the measurement water (e.g., ion-change water) supplied thereinto to an additional flow passage other than the measurement-water flow passage.

Further, if the plates are made of different materials and directly jointed to each other while defining the flow passages therebetween, a concentration of eluates from the materials is likely to increase, and/or the influence of carbon dioxide gas to be transferred is likely to become far more serious. Thus, an adhesive organic film may be at least partially interposed between respective joint surfaces of the plates.

As above, in the total organic carbon measurement apparatus of the present invention, the aqueous-sample flow passage, the gas permeable membrane, the measurement-water flow passage and the conductivity measuring electrode are defined between and incorporated in the plurality of laminated plates. This makes it possible to integrate the carbon-dioxide separation unit and the conductivity measurement unit together so as to facilitate reduction in size of the apparatus and perform a TOC measurement in a relatively low flow rate.

The above total organic carbon measurement apparatus may have the oxidizing flow passage defined by further laminating thereon the fourth plate made of a material transparent to ultraviolet light. This makes it possible to integrate the organics oxidation unit with the carbon-dioxide separation unit and the conductivity measurement unit so as to further reduce the size of the apparatus, and quickly perform the TOC measurement just after the conversion to carbon dioxide so as to achieve enhanced measurement accuracy.

The second and third plates may be arranged to define therebetween the branch flow passage for guiding a part of the measurement water (e.g., ion-exchanged water) supplied thereinto to an additional flow passage other than the measurement-water flow passage. This makes it possible to supply the measurement water at an adjust flow rate while maintaining a flow rate of circulating water at an optimal value for background characteristics thereof.

The adhesive organic film may be interposed between respective joint surfaces of the plates forming the each of the units, and each of the flow passages may be defined to fluidically communicate with a through-hole formed in each of the plates. This makes it possible to eliminate the need for connecting between the units using various pipes made of different materials, so as to reduce the influence of contaminant due to elution of the pipe materials or the like and minimize a dead volume between the units to allow the TOC measurement to be performed with higher sensitivity and enhanced efficiency.

DESCRIPTION OF THE EXEMPLARY EMBODIMENTS

With reference to the drawings, an embodiment of the present invention will now be specifically described.

Figure 1:
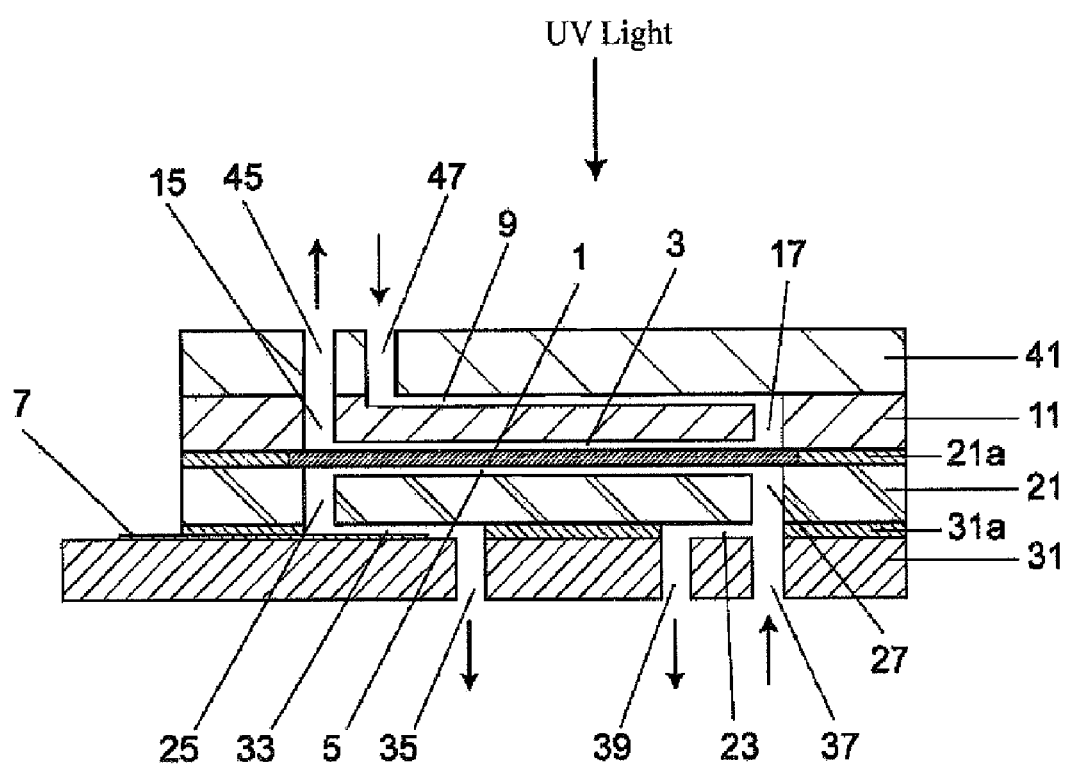
FIG. 1 is a sectional view showing a TOC measurement apparatus according to one embodiment of the present invention.

FIG. 1 is a sectional view showing a total organic carbon (TOC) measurement apparatus according to one embodiment of the present invention.

The TOC measurement apparatus according to this embodiment comprises an organics oxidation unit, a conductivity measurement unit, and a carbon-dioxide separation unit sandwiched between the organics oxidation unit on an upper side and the conductivity measurement unit on a lower side.

The carbon-dioxide separation unit includes a gas permeable membrane 1, a first plate 11 and a second plate 21 which are laminated and fixed to each other in such a manner that an aqueous-sample flow passage 3 is defined between the first plate 11 and the gas permeable membrane 1, and a measurement-water flow passage 5 is defined between the second plate 21 and the gas permeable membrane 1 and in opposed relation to the aqueous-sample flow passage 3 through the gas permeable membrane 1.

The conductivity measurement unit includes a third plate 31 fixedly attached to the second plate 21 in opposed relation thereto in such a manner that the third and second plates 31, 21 are arranged to define therebetween a measurement cell in fluid communication with the measurement-water flow passage 5, and a conductivity measuring electrode 7 disposed in the measurement cell. A flow passage 33 in the measurement cell has one end in fluid communication with the measurement-water flow passage 5 through a through-hole 25, and the other end in fluid communication with a discharge port 35 formed in the third plate 31 as a through-hole.

The third plate 31 is formed with a through-hole serving as a supply port 37 for measurement water. The supply port 37 is in fluid communication with the measurement-water flow passage 5 through a through-hole 27 formed in the second plate 21, and in fluid communication with a through-hole formed in the third plate 31 to serve as a discharge port 39, through a branch flow passage 23 defined between the second and third plates 21, 31.

The organics oxidation unit includes a fourth plate 41 fixedly attached to the first plate 11 in opposed relation thereto. The fourth and first plates 41, 11 are arranged to define therebetween an oxidizing flow passage 9, and the fourth plate 41 is made of a transparent material which allows external ultraviolet light to enter at least a part of the oxidizing flow passage 9.

The oxidizing flow passage 9 has one end (first end) in fluid communication with a through-hole formed in the fourth plate 41 to serve as a supply port 47 for an aqueous sample, and the other end (second end) in fluid communication with the aqueous-sample flow passage 3 through a through-hole 17 formed in the first plate 11. The aqueous-sample flow passage 3 is in fluid communication with a through-hole 15 formed in the first plate 11 to discharge the aqueous sample, and a through-hole formed in the fourth plate 41 to serve as a discharge port 45.

Figure 2:
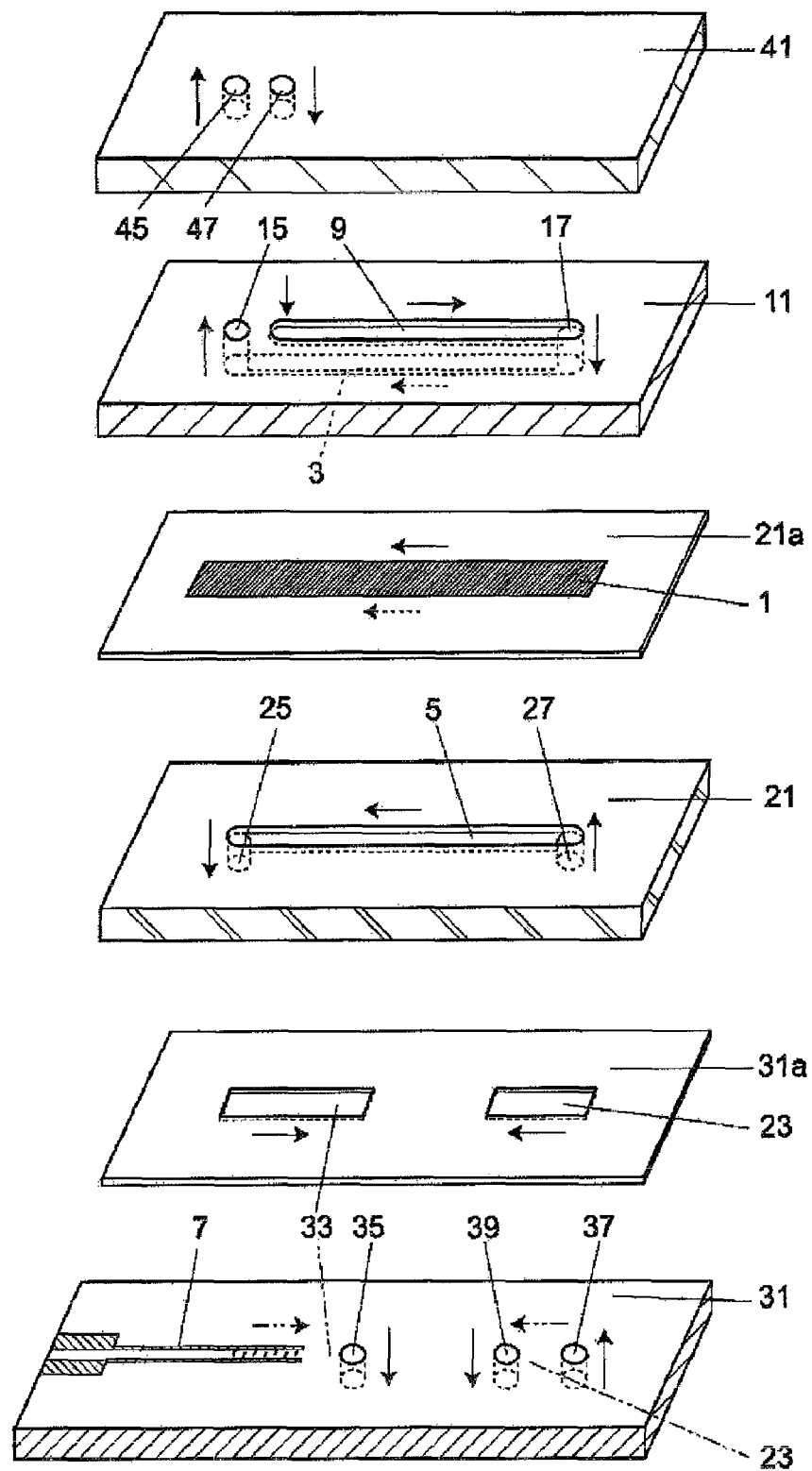
FIG. 2 is an exploded perspective view showing a plurality of plates in the TOC measurement apparatus according to the embodiment.

With reference to FIG. 2, details of the respective structures of the units and a production process of the TOC measurement apparatus will be described below. FIG. 2 is an exploded perspective view showing respective components of the TOC measurement apparatus in FIG. 1.

[Carbon-Dioxide Separation Unit]

The carbon-dioxide separation unit is a region for transmitting or transferring organic carbon which has been oxidized and converted to carbon dioxide on the side of the aqueous-sample flow passage 3, to the side of the measurement-water flow passage 5. The carbon-dioxide separation unit comprises the gas permeable membrane 1, and the aqueous-sample and measurement-water flow passages 3, 5 defined by the gas permeable membrane 1 and the first and second plates 11, 21 located on respective opposite sides of the gas permeable membrane 1.

The aqueous-sample flow passage 3 may be provided by forming a micro-groove (width: 0.01 to 10 mm, depth: 0.01 to 0.5 mm, length: several mm to several hundred mm) in a lower surface of the first plate 11. For example, the groove may have a width of 1 mm, a depth of 0.2 mm and a length of 200 mm. The aqueous-sample flow passage 3 may be formed based on a microfabrication technique using a wet etching process, a dry etching process or a sandblasting process.

The measurement-water flow passage 5 may be provided by forming a micro-groove (width: 0.01 to 10 mm, depth: 0.01 to 0.5 mm, length: several mm to several hundred mm) in an upper surface of the second plate 21. For example, the groove may have a width of 1 mm, a depth of 0.2 mm and a length of 200 mm. The measurement-water flow passage 5 may be formed based on the same fabrication technique as that for the aqueous-sample flow passage 3.

The gas permeable membrane 1 is preferably formed of a hydrophobic porous membrane. For example, a porous fluororesin membrane (e.g., Poreflon® produced by Sumitomo Electric Industries, Ltd.) may be used.

[Organics Oxidation Unit]

The organics oxidation unit is a region for oxidizing organics in the aqueous sample by irradiation of ultraviolet light. The organics oxidation unit comprises the oxidizing flow passage 9 defined between the fourth plate 41 and the first plate 11.

The oxidizing flow passage 9 may be provided by forming a micro-groove (width: 0.01 to several mm, depth: 0.01 to 1 mm, length: 100 mm to several thousand mm) in an upper surface of the first plate 11. For example, the groove may have a width of 1 mm, a depth of 0.2 mm and a length of 200 mm. The oxidizing flow passage 9 may be formed based on a microfabrication technique using a wet etching process, a dry etching process or a sandblasting process.

For example, a quartz plate may be used as the fourth plate 41 which is transparent to ultraviolet light, and a silicon plate covered by an oxide film may be used as the first plate 11. These plates 41, 11 can be readily joined to each other by a joining process using hydrofluoric acid.

The supply and discharge ports 47, 45 for supplying and discharging the aqueous sample into/from the apparatus are pre-formed in the fourth plate 41, and the through-holes 17, 15 for guiding the aqueous sample through the apparatus are pre-formed in the first plate 11. For example, each of these supply and discharge ports and the through-holes may be formed by a sandblasting process. The first end of the oxidizing flow passage 9 is positioned relative to the aqueous-sample supply port 47, and the second end of the oxidizing flow passage 9 is fluidically connected to the aqueous-sample through-hole 17. The aqueous-sample through-hole 15 is formed at a position corresponding to the aqueous-sample discharge port 45.

Organics in the aqueous sample is irradiated with ultraviolet light from above the fourth plate 41, and converted to carbon dioxide. Just after the conversion, the aqueous sample with the carbon dioxide can be fed to the aqueous-sample flow passage 3 to quickly perform the TOC measurement. This makes it possible to achieve enhanced measurement accuracy.

[Conductivity Measurement Unit]

The conductivity measurement unit is a region for detecting carbon dioxide transferred to the side of the measurement-water flow passage 5. The measuring electrode 7 is located at a central position of the conductivity measurement unit, and disposed in the flow passage in the measurement cell.

The measuring electrode 7 is formed on the third plate 31. For example, the third plate 31 is made of quartz, and the measuring electrode 7 is formed on the quartz plate 31 as a comb-shaped electrode pattern of a Pt/Ti film (wherein a Pt film is formed on a Ti film to provide enhanced adhesion) by a conventional film forming technique using a combination of a photolithographic process and a sputtering process. An adhesive thin-film sheet 31*a* made, for example, of PDMS (poly-dimethylsiloxane: e.g., Sylgard 184® produced by Corning Inc.), which has two cutouts corresponding to the branch flow passage 23 and the electrode flow passage 33, is attached onto an upper surface of the third plate 31 including a part of an upper surface of the measuring electrode 7. Then, the second plate 21 formed with the through-holes 27, 25 and the groove serving as the measurement-water flow passage 5 is joined to the third plate 31 so as to cover thereover.

The third plate 31 has the aqueous-sample supply port 37 formed at a position corresponding to the through-hole 27. The third plate 31 further has the branch flow passage 23 and the discharge port 39 which are located adjacent to the aqueous-sample supply port 37 to guide and discharge an excess part of the measurement water. Thus, a flow rate of the measurement water to be introduced into the flow passage 33 on the measuring electrode 7 can be adjusted to supply the measurement water while maintaining a flow rate of the circulating water at an optimal value for background characteristics thereof.

A PDMS film, an adhesive organic film or a thin film sheet 31*a* applied with an adhesive can be used for providing a gap between the second and third plates 21, 31 so as to achieve the branch flow passage 23 and the electrode flow passage 33 defined between the second and third plates 21, 31. Preferably, each of the flow passages 23, 33 has a depth of 10 to 1000 μm. In this embodiment, the depth of each of the flow passages 23, 33 is set at about 100 μm.

Each of the through-holes 25, 27, the supply port 37 and the discharge ports 35, 37 formed in the second and third plates 21, 31 may be formed by a sandblasting process.

As the last step, the first plate 11 and the second plate 21 are joined together in such a manner as to allow the carbon-dioxide separation unit to be sandwiched between the organics oxidation unit and the conductivity measurement unit, while sealing an outer periphery of the gas permeable membrane 1 by a thin film 21*a* made of PDMS, to provide a TOC measurement having the carbon-dioxide separation unit and the conductivity measurement unit which are integrated together. This makes it possible to facilitate reduction in size of the apparatus and perform the TOC measurement in a relatively low flow rate.

In this embodiment, the components, such as the plates, of the TOC measurement apparatus, are made of silicon, quartz, PDMS (poly-dimethylsiloxane) and porous fluororesin, which are materials having almost no problem about elution and others. This makes it possible to eliminate the need for connecting between the units using various pipes made of different materials, so as to reduce the influence of contaminant due to elution of the pipe materials or the like and minimize a dead volume between the units to allow the TOC measurement to be performed with higher sensitivity and enhanced efficiency.

With reference to FIG. 1, an operation of measuring a concentration of organics using the TOC measurement apparatus according to this embodiment will be described below.

In the following example, an aqueous solution of potassium hydrogen phthalate was used as an aqueous sample, and ion-exchanged water was used as measurement water, by way of example.

The aqueous sample was supplied from the supply port 47 to the oxidizing flow passage 9 at a flow rate of about 0.1 mL/min. The aqueous sample was irradiated with ultraviolet light for 0.1 to 5 minutes, preferably 3 minutes to oxidize organics in the aqueous sample, and carbon dioxide converted from the organics was dissolved in the aqueous sample.

The ion-exchanged water was created by an ion-exchange water refiner, and supplied from the supply port 37 at a flow rate of 0.1 to 10 mL/min (in this example, 2 mL/min). A flow rate of the measurement water suitable for the conductivity measurement is a relatively low value. Thus, an excess part of the ion-exchanged water (i.e., circulating water) supplied from the supply port 37 was discharged from the discharge port 39 through the branch flow passage 23 to adjust a flow rate of the measurement water. Based on the newly provided branch flow passage 23 and discharge port 39, a flow rate of the ion-exchanged water in a circulating system could be set at an optimal value (e.g., 1.9 mL/min) while ensuring an optimal flow rate (e.g., 0.1 mL/min) of the measurement water (i.e., ion-exchanged water for the conductivity measurement).

The aqueous sample having the carbon dioxide converted from the organics and dissolved therein was fed to the aqueous-sample flow passage 3 through the through-hole 17. Then, the carbon dioxide in the aqueous sample was transferred from the aqueous-sample flow passage 3 to the measurement-water flow passage 5 through the gas permeable membrane 1, and dissolved in the ion-exchanged water (i.e., measurement water).

After releasing the carbon dioxide gas through the gas permeable membrane 1, the aqueous sample was discharged from the discharge port 45 through the through-hole 15. The measurement water absorbing the carbon dioxide was fed to the measurement cell through the through-hole 25. The measurement water was guided through the flow passage 33 to measure a conductivity of the ion-exchanged water by the measuring electrode 7.

An aqueous sample free of organics and carbon dioxide was used for measuring a background conductivity. The background conductivity was subtracted from the above actually measured conductivity to quantitatively determine a concentration of the carbon dioxide, and the carbon dioxide concentration was converted to a TOC content.

The above embodiment has been described as one example of the present invention. Therefore, in the TOC measurement apparatus of the present invention, a material of each component, such as the plates and the sealing film, is not limited to a specific one described in the above embodiment, but may be any other suitable material capable of achieving an equivalent function. Further, the TOC measurement apparatus of the present invention is not limited to the specific structure of the above embodiment comprising the four plates 11, 21, 31, 41. For example, the TOC measurement apparatus may be made up of only the three plates 11, 21, 31, or may be made up of only the two plates 11, 21. In the TOC measurement apparatus made up of only the three plates 11, 21, 31, the same operation as that in the above embodiment can be achieved by pre-converting organic in an aqueous sample to carbon dioxide, and then introducing the carbon dioxide-containing aqueous sample from the through-hole 17.

In the above embodiment, the comb-shaped measuring electrode has been employed. Alternatively, any other suitable type of measuring electrode may be used. For example, a pair of plate electrodes may be provided, respectively, in the second plate 21 and the third plate 31 to form a parallel plate measuring electrode.

The arrangement of the plates is not limited to the vertical arrangement in the above embodiment, but the plates may be arranged in a horizontal direction. For example, the fourth plate and the third plate may be disposed adjacent, respectively, to the first plate and the second plate, in such a manner as to be aligned therewith in a horizontal direction. In this case, the height dimension of the apparatus can be reduced.

In cases where inorganic carbon is contained in an aqueous sample, a total carbon content can be determined by the measurement in the above embodiment. When it is necessary to exactly determine a content of organic carbon, it may be obtained by subtracting a value of inorganic carbon content determined without irradiation of ultraviolet light from a value of total carbon content determined after irradiation of ultraviolet light.

INDUSTRIAL APPLICABILITY

The present invention can be utilized for a total organic carbon measurement apparatus for determining organic contamination in low-impurity water, called "pure water" or "ultra-pure water".

What is claimed is:

1. A total organic carbon measurement apparatus comprising:

an organics oxidation unit for oxidizing and converting organics in an aqueous sample supplied thereinto, to carbon dioxide;

a carbon-dioxide separation unit for transferring the carbon dioxide in the aqueous sample after passing through said organics oxidation unit, to measurement water; and a conductivity measurement unit for measuring a conductivity of the measurement water from said carbon-dioxide separation unit, wherein said carbon-dioxide separation unit includes a gas permeable membrane, a first plate and a second plate which are laminated and fixed to each other in such a manner that an aqueous-sample flow passage is defined between said first plate and said gas permeable membrane, and a measurement-water flow passage is defined between said second plate and said gas permeable membrane and in opposed relation to said aqueous-sample flow passage through said gas permeable membrane;

wherein said conductivity measurement unit includes a third plate fixedly attached to said second plate in opposed relation thereto in such a manner that said third and second plates are arranged to define therebetween a measurement cell including an electrode flow passage in fluid communication with said measurement-water flow passage; and a conductivity measuring electrode disposed in said measurement cell;

wherein the third plate includes a supply port for supplying the ion-exchanged measurement water to the measurement-water flow passage and to a branch flow passage, a first discharge port that discharges a first part of the ion-exchanged measurement water that has passed through both the measurement-water flow passage and the electrode flow passage and a second discharge port;

wherein said second and third plates are arranged to define therebetween the branch flow passage for guiding a second part of the ion-exchanged measurement water supplied via the supply port to the second discharge port; and wherein the carbon dioxide in the aqueous sample is transferred from the aqueous-sample flow passage to the measurement-water flow passage through the gas permeable membrane and dissolved in the first part of the ion-exchanged measurement water.

2. The total organic carbon measurement apparatus as defined in claim 1, wherein said organics oxidation unit includes a fourth plate fixedly attached to said first plate in opposed relation thereto, wherein said fourth and first plates are arranged to define therebetween an oxidizing flow passage in fluid communication with said aqueous-sample flow passage, and said fourth plate is made of a transparent material which allows external ultraviolet light to enter at least a part of said oxidizing flow passage, whereby organics in the aqueous sample is oxidized by irradiation of ultraviolet light.

3. The total organic carbon measurement apparatus as defined in claim 1, which includes an adhesive organic film at least partially interposed between respective joint surfaces of said plates.

4. The total organic carbon measurement apparatus as defined in claim 2, which includes an adhesive organic film at least partially interposed between respective joint surfaces of said plates.

5. The total organic carbon measurement apparatus as defined in claim 1, wherein the second discharge port is located adjacent to the supply port.

* * * * *